Oct. 29, 1963 E. S. BOERNER Plant Pat. 2,294
ROSE PLANT
Filed Sept. 24, 1962
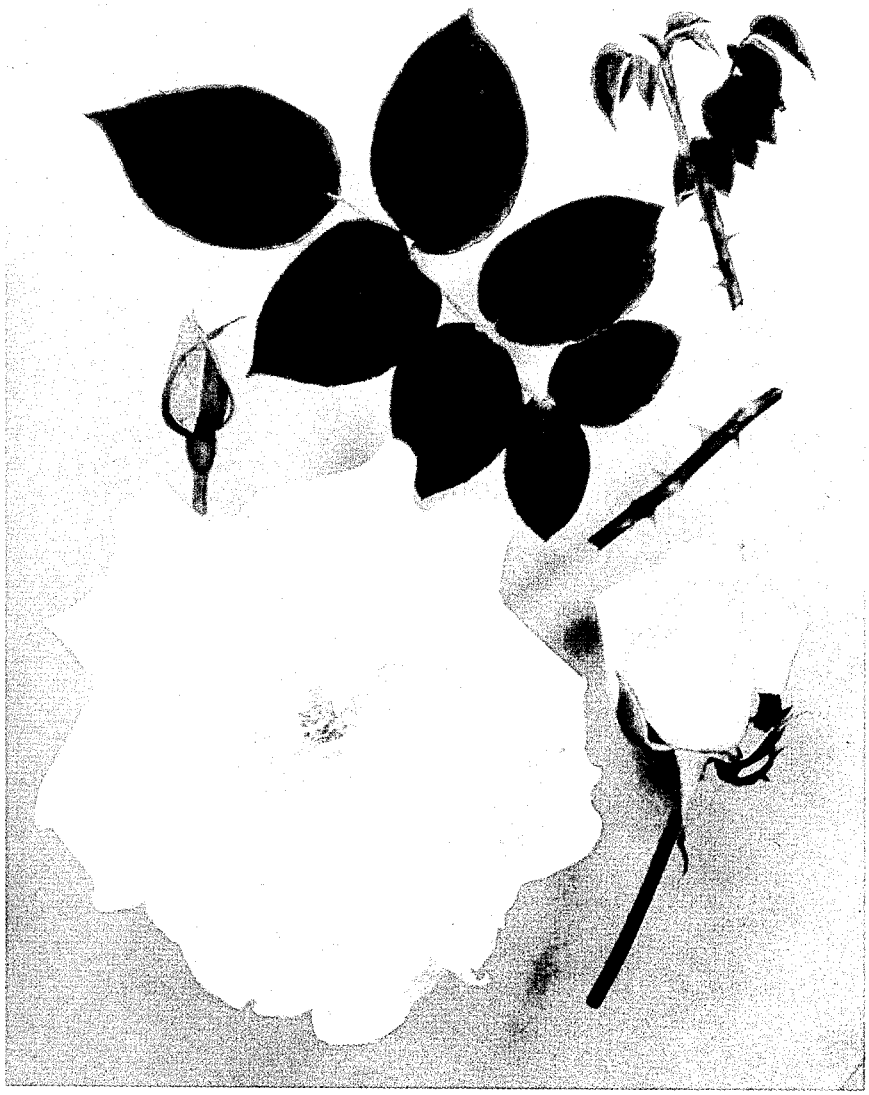
Inventor.
E. S. Boerner
By: Robb & Robb
Attorneys.

United States Patent Office

Plant Pat. 2,294
Patented Oct. 29, 1963

2,294
ROSE PLANT

Eugene S. Boerner, Newark, N.Y., assignor to Jackson & Perkins Company, Newark, N.Y., a corporation of New York Filed Sept. 24, 1962, Ser. No. 225,949
1 Claim. (Cl. Plt.—18)

The present invention relates to a new and distinct variety of rose plant of the hybrid tea class, which was originated by me by crossing an unnamed and unpatented seedling of "Serenade" (Plant Patent No. 852) with the variety known as "Kate Smith" (Plant Patent No. 1,317).

The primary objective of this breeding was to produce a new rose variety that is different, but which would be suitable as a companion for the variety known as "Golden Masterpiece" (Plant Patent No. 1,284), with particular regard for a large flower size. This objective was fully achieved, along with other desirable improvements, as evidenced by the following unique combination of characteristics which are outstanding in the new variety and which distinguish it from its parents, as well as from all other varieties of which I am aware:

(1) A vigorous habit of plant growth;
(2) Healthy foliage;
(3) Ovoid pointed buds, and high-centered flowers which make the new variety a good show rose;
(4) A large open flower size; and
(5) A distinctive and attractive general color tonality of the flowers corresponding to La France Pink, lightly overcast with Shrimp Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Serenade."
*Pollen parent.*—"Kate Smith."

Classification:
*Botanic.*—Hybrid tea.
*Commercial.*—Hybrid tea.

*Flower*

(Observations made from specimens grown outdoors at Newark, New York, in the early morning, during the middle of the month of September.)

Blooming habit: Recurrent—continuous.

Bud:
*Size.*—Very large.
*Form.*—Ovoid; pointed; is not affected by wet or hot weather.
*Color.*—When sepals first divide—Old Rose, Plate 13. When petals begin to unfurl—Geranium Pink, Plate 1. When half-blown: inside of petals—Eosine Pink, Plate 1, very lightly overcast with Orient Pink, Plate 2; reverse of petals—Shrimp Pink, Plate 1, with outer edge of petals overcast with Eosine Pink, Plate 1.
*Sepals.*—Slightly branched; curl back when petals begin to unfurl. Color: inside—Pale Turtle Green, Plate 32; outside—Chromium Green, Plate 32.
*Calyx.* — Color — Chromium Green, Plate 32. Shape — pear. Size — large. Aspect. — smooth. Odor when rubbed—none.
*Peduncle.*—Length — medium. Aspect — smooth. Strength — erect; heavy. Color — Cress Green, Plate 31.
*Opening.*—Opens up well; is not affected by adverse weather conditions.

Bloom:
*Size.*—Very large. Average size when fully expanded—6 inches.
*Borne.*—Singly.
*Stems.*—Medium length; strong.
*Form (when first open).*—High-centered. Permanence—retains its form to the end, but outer petals curl back.
*Petalage.*—Double (full but open center). Number of petals under normal conditions—from 35 to 40.
*Color.*—Center of flower—Orient Pink, Plate 2, lightly overcast on the outer edge of the petals with Eosine Pink, Plate 1, and with the center of the flower lightly overcast with La France Pink, Plate 1. Outer petals—Seashell Pink, Plate 14, lightly overcast with La France Pink, Plate 1, on the outer edge of the petals. Base of petals (aiglet)—Citron Yellow, Plate 16. Inside of petals—La France Pink, Plate 1, lightly overcast with Shrimp Pink, Plate 1. Reverse of petals—Seashell Pink, Plate 14, very lightly overcast with Hermosa Pink, Plate 1. General tonality from a distance—La France Pink, Plate 1, lightly overcast with Shrimp Pink, Plate 1.
*Discoloration.*—General tonality at end of first day—La France Pink, Plate 1, lightly overcast with Shrimp Pink, Plate 1. Second day—La France Pink, Plate 1, very lightly overcast with Shrimp Pink, Plate 1. Third day—La France Pink, Plate 1, very lightly overcast with Shrimp Pink, Plate 1.

Petals:
*Texture.*—Thick; is not affected by wet or hot weather.
*Appearance.*—Inside—satiny. Outside—shiny.
*Form.*—Oval.
*Arrangement.* — Imbricated (regularly arranged shingle-like).
*Petaloids in center.*—Few; large.
*Persistance.*—Drop off cleanly.
*Fragrance.*—Moderate. Nature—tea (average hybrid tea scent).
*Lasting quality.* — On the plant—long. As cut flower—long.

*Genital Organs*

Stamens, anthers: Medium size; many; regularly arranged aroundstyles. Color—Empire Yellow, Plate 4.
Stamens, filaments (threads): Medium length. Color—Pinard Yellow, Plate 4.
Pollen: Color—Maize Yellow, Plate 4.
Styles: Loosely separated; uneven medium length; thin.
Stigmas: Color—Light Buff, Plate 15.
Ovaries: All enclosed in calyx.
Hips: None.
Seeds: None.

*Plant*

Form: Bush.
Growth: Vigorous; upright.
Foliage: Compound of 3–7 leaflets.
*Size.*—Very large; healthy.
*Quantity.*—Normal.

*Color.*—New foliage: upper side—Van Dyke Red, Plate 13; under side—Roman Green, Plate 16, lightly overcast with Acajou Red, Plate 13. Old foliage: upper side—Empire Green, Plate 32; under side—Light Cress Green, Plate 31.

*Shape.*—Oval pointed.

*Texture.*—Upper side—leathery. Under side—smooth.

*Ribs and veins.*—Ordinary.

*Edge.*—Serrated (saw-toothed).

*Serration.*—Single; small.

*Leaf stem.*—Color—Absinthe Green, Plate 31. Under side—prickly.

*Stipules.*—Medium length; smooth.

Wood:

*New wood.*—Color—Biscay Green, Plate 17. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; medium length; straight. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a vigorous habit of plant growth, healthy foliage, ovoid pointed buds and high-centered flowers, a large flower size, and a distinctive and attractive general color tonality of the flowers corresponding to La France Pink, lightly overcast with Shrimp Pink.

No references cited.